United States Patent
Brief et al.

(10) Patent No.: US 10,905,371 B2
(45) Date of Patent: Feb. 2, 2021

(54) AUTOMATIC DETECTION OF HUMAN PHYSIOLOGICAL PHENOMENA

(71) Applicant: my.Flow, Inc., San Jose, CA (US)

(72) Inventors: Amanda Karen Brief, San Francisco, CA (US); Madeeha Ghori, Mountain View, CA (US); Katie Chen, Berkeley, CA (US); Tomas Alfonso Vega Galvez, Berkeley, CA (US); Drake Myers, Berkeley, CA (US); Jacob David Schatz McEntire, Elkins Park, PA (US)

(73) Assignee: my.Flow, Inc., San Jose, CA (US)

( * ) Notice: Subject to any disclaimer, the term of this patent is extended or adjusted under 35 U.S.C. 154(b) by 570 days.

(21) Appl. No.: 15/154,687

(22) Filed: May 13, 2016

(65) Prior Publication Data

US 2017/0150917 A1    Jun. 1, 2017

Related U.S. Application Data

(60) Provisional application No. 62/260,583, filed on Nov. 29, 2015.

(51) Int. Cl.
*A61B 5/00* (2006.01)
*A61F 13/84* (2006.01)
(Continued)

(52) U.S. Cl.
CPC ............ *A61B 5/4318* (2013.01); *A61B 5/002* (2013.01); *A61B 5/0022* (2013.01); *A61B 5/026* (2013.01);
(Continued)

(58) Field of Classification Search
CPC ..... A61B 5/4318; A61B 5/002; A61B 5/6808; A61B 5/02042; A61B 5/742; A61B 5/7225; A61B 5/0022; A61B 5/026; A61B 2560/0443; A61B 2560/0406; A61B 2560/0266; A61B 2562/227;
(Continued)

(56) References Cited

U.S. PATENT DOCUMENTS 5,313,722 A * 5/1994 Ackerman ............. B42D 5/047
283/4
6,063,042 A * 5/2000 Navot ..................... A61F 13/42
600/584
(Continued)

*Primary Examiner* — Jacqueline Cheng
*Assistant Examiner* — Tho Q Tran

(57) ABSTRACT

Introduced here is technology to monitor moisture levels in a hygiene product, such as tampons, pads, menstrual cups, child diapers, adult diapers etc. According to one embodiment, a moisture sensor is inserted inside a feminine hygiene product. The moisture sensor is connected to a wearable device that gathers the moisture data and sends the data to a mobile device, such as a cell phone. The cell phone generates notifications to the user, such as percentage saturation of the feminine hygiene product, message to change the feminine hygiene product, expected start and end dates of the next menstrual cycle, etc. According to another embodiment, the moisture sensor can be inserted in other hygiene products, such as child diapers or adult diapers, to measure the amount of urination, defecation, or other excretions, and to generate notifications to the user, the user's caretaker, or a third party.

22 Claims, 20 Drawing Sheets

(51) Int. Cl.
*A61B 5/026* (2006.01)
*A61B 5/02* (2006.01)

(52) U.S. Cl.
CPC ........ *A61B 5/02042* (2013.01); *A61B 5/6808* (2013.01); *A61B 5/7225* (2013.01); *A61B 5/742* (2013.01); *A61F 13/84* (2013.01); *A61B 2560/0266* (2013.01); *A61B 2560/0406* (2013.01); *A61B 2560/0443* (2013.01); *A61B 2562/029* (2013.01); *A61B 2562/227* (2013.01); *A61F 2013/8473* (2013.01)

(58) Field of Classification Search
CPC ............... A61B 2562/029; A61F 13/84; A61F 2013/8473; A61F 13/42
USPC .......................................... 600/551, 371, 362
See application file for complete search history.

(56) References Cited

U.S. PATENT DOCUMENTS

| | | | | |
|---|---|---|---|---|
| 8,229,535 | B2* | 7/2012 | Mensinger | A61B 5/7445 600/345 |
| 2003/0144602 | A1* | 7/2003 | Jennings | A61B 10/0012 600/551 |
| 2004/0128153 | A1* | 7/2004 | Zhang | A61B 5/4277 600/584 |
| 2005/0143788 | A1* | 6/2005 | Yun | A61K 31/137 607/46 |
| 2007/0021815 | A1* | 1/2007 | Kaiser | A61B 5/024 607/141 |
| 2007/0049881 | A1* | 3/2007 | Ales, III | A61F 13/42 604/361 |
| 2007/0123754 | A1* | 5/2007 | Cuddihy | A61B 5/1113 600/300 |
| 2008/0096726 | A1* | 4/2008 | Riley | A63B 24/0006 482/8 |
| 2010/0241094 | A1* | 9/2010 | Sherron | A61F 13/42 604/361 |
| 2010/0305530 | A1* | 12/2010 | Larkin | A61F 13/2051 604/361 |
| 2012/0040655 | A1* | 2/2012 | Larkin | A61B 5/0002 455/418 |
| 2013/0018231 | A1* | 1/2013 | Hong | A61F 13/42 600/300 |
| 2015/0121462 | A1* | 4/2015 | Courage | H04L 63/08 726/4 |
| 2015/0217019 | A1* | 8/2015 | Martello | A61F 13/42 604/359 |
| 2015/0357728 | A1* | 12/2015 | Chen | H01R 4/48 439/725 |

* cited by examiner

AUTOMATIC DETECTION OF HUMAN PHYSIOLOGICAL PHENOMENA

CROSS-REFERENCE TO RELATED APPLICATIONS

This application claims priority to the U.S. provisional patent application Ser. No. 62/260,583 filed Nov. 29, 2015, which is incorporated herein by reference in its entirety.

TECHNICAL FIELD

The present application is related to an automatic detection of human physiological phenomena, and more specifically to methods and systems that measure properties associated with human excretion.

BACKGROUND

Most women today use traditional feminine hygiene products such as tampons, panty liners, and sanitary napkins during their menstrual cycle. With traditional feminine hygiene products, women do not know when the feminine hygiene product is full, unless they visually inspect the feminine hygiene product. Forgetting to check the feminine hygiene product can result in embarrassing bloodstained clothing. Further, keeping track of how long the tampon has been inserted in the body is difficult, and if the tampon has been inserted for a sufficiently long time, the tampon can cause lethal toxic shock syndrome.

SUMMARY

Introduced here is technology to monitor moisture levels in a hygiene product, such as tampons, sanitary napkins, menstrual cups, child diapers, adult diapers, etc. According to one embodiment, a moisture sensor is inserted inside a feminine hygiene product, such as a tampon, a sanitary napkin, or a menstrual cup. The moisture sensor is connected to a wearable device which gathers the moisture data and sends it to a mobile device, such as a cell phone. The cell phone generates notifications to the user, such as percentage of saturation of the feminine hygiene product, message to change the feminine hygiene product, expected start and end dates of the next menstrual cycle, etc. According to another embodiment, the moisture sensor can be inserted in other hygiene products, such as child diapers or adult diapers, to measure the amount of urination, defecation, or other excretions, and to generate notifications to the user, the user's caretaker, or a third party, such as a doctor.

BRIEF DESCRIPTION OF THE DRAWINGS

These and other objects, features and characteristics of the present embodiments will become more apparent to those skilled in the art from a study of the following detailed description in conjunction with the appended claims and drawings, all of which form a part of this specification. While the accompanying drawings include illustrations of various embodiments, the drawings are not intended to limit the claimed subject matter.

DETAILED DESCRIPTION

Terminology

Figure 1:
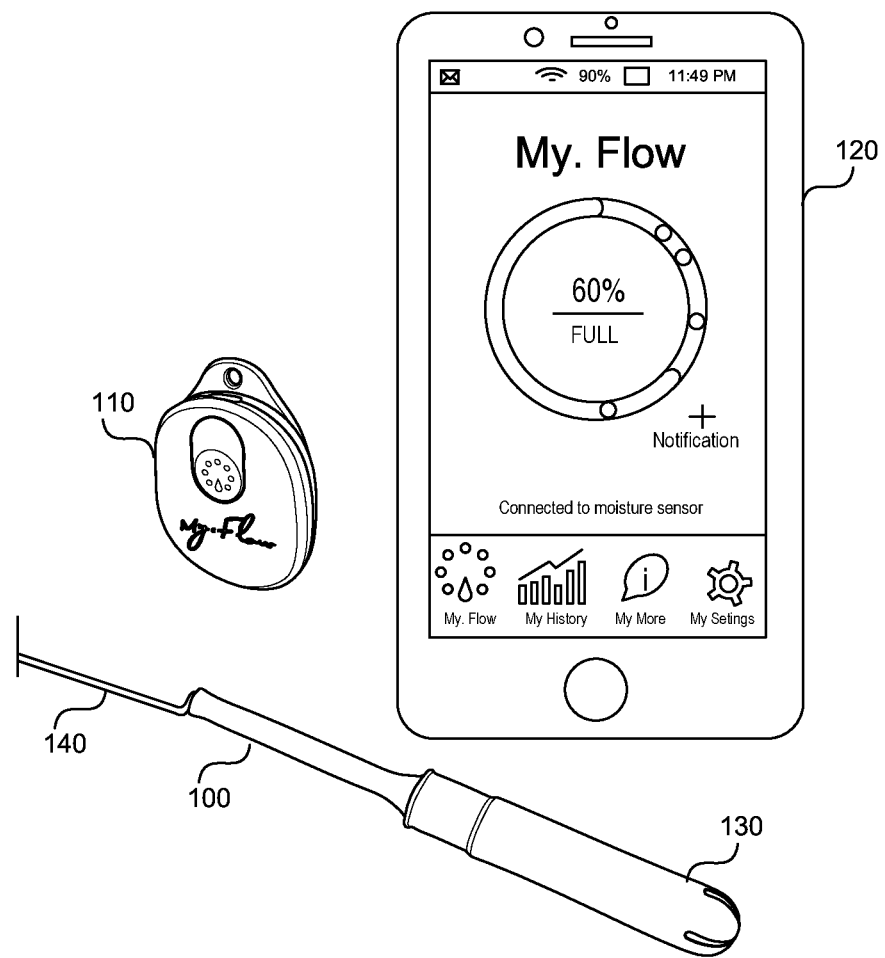
FIG. 1 shows the components of a feminine hygiene product to monitor blood flow during a menstrual cycle, according to one embodiment.

Brief definitions of terms, abbreviations, and phrases used throughout this application are given below.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described that may be exhibited by some embodiments and not by others. Similarly, various requirements are described that may be requirements for some embodiments but not others.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, mean any connection or coupling, either direct or indirect, between two or more elements. The coupling or connection between the elements can be physical, logical, or a combination thereof. For example, two devices may be coupled directly, or via one or more intermediary channels or devices. As another example, devices may be coupled in such a way that information can be passed therebetween, while not sharing any physical connection with one another. Additionally, the words "herein," "above," "below," and words of similar import, when used in this application, shall refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

If the specification states a component or feature "may," "can," "could," or "might" be included or have a characteristic, that particular component or feature is not required to be included or have the characteristic.

The term "module" refers broadly to software, hardware, or firmware components (or any combination thereof). Modules are typically functional components that can generate useful data or another output using specified input(s). A module may or may not be self-contained. An application program (also called an "application") may include one or more modules, or a module may include one or more application programs.

The terminology used in the Detailed Description is intended to be interpreted in its broadest reasonable manner, even though it is being used in conjunction with certain examples. The terms used in this specification generally have their ordinary meanings in the art, within the context of the disclosure, and in the specific context where each term is used. For convenience, certain terms may be highlighted, for example using capitalization, italics, and/or quotation marks. The use of highlighting has no influence on the scope and meaning of a term; the scope and meaning of a term is the same, in the same context, whether or not it is highlighted. It will be appreciated that the same element can be described in more than one way.

Consequently, alternative language and synonyms may be used for any one or more of the terms discussed herein, but special significance is not to be placed upon whether or not a term is elaborated or discussed herein. A recital of one or more synonyms does not exclude the use of other synonyms. The use of examples anywhere in this specification, including examples of any terms discussed herein, is illustrative only and is not intended to further limit the scope and meaning of the disclosure or of any exemplified term. Likewise, the disclosure is not limited to various embodiments given in this specification.

Technology

FIG. 1 shows the components of a feminine hygiene product to monitor blood flow during a menstrual cycle, according to one embodiment. The feminine hygiene product 100, such as a tampon, a panty liner, a sanitary napkin, a sanitary brief, a menstrual cup, etc., includes an absorbent part 130 configured to collect blood, and a string 140 attached to the absorbent part 130. The string 140 encloses a plurality of conductive wires coupled to a sensor disposed within the absorbent part 130. A wearable device 110 is coupled to the string 140, and receives data from the sensor regarding an amount of blood associated with the menstrual cycle of a user. The sensor can be a moisture sensor, a piezo sensor, a temperature sensor, etc. The wearable device 110 communicates with another electronic device 120 comprising a display, such as a cell phone, a desktop computer, a personal digital assistant, a tablet, a wearable, etc., via a wireless connection such as a Bluetooth. The wearable device 110 sends data regarding the amount of blood flow, a notification to display to the user, etc. to the electronic device 120.

Figure 2A:
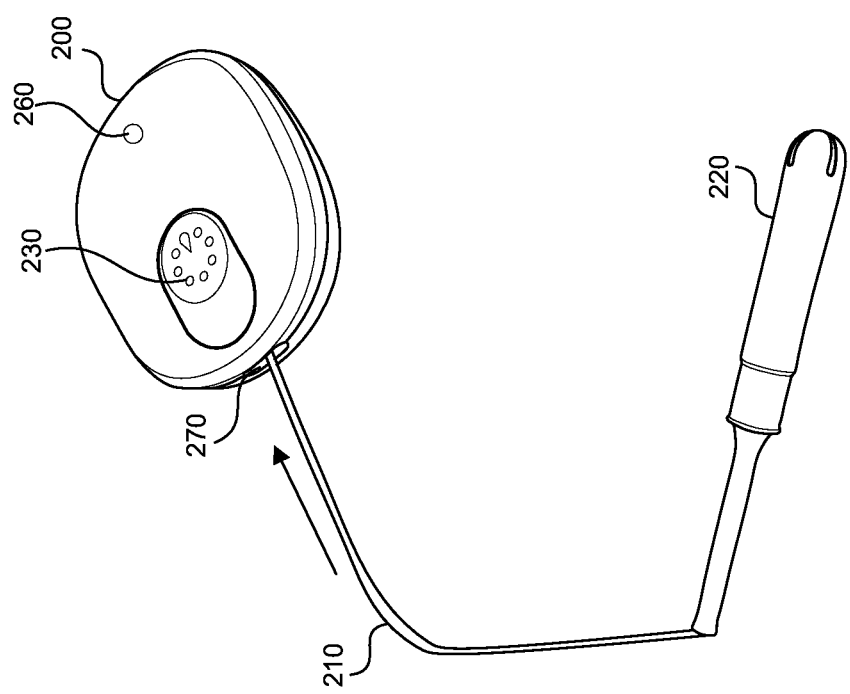
FIGS. 2A-2B show a string engaging with the wearable device, according to one embodiment.
Figure 2B:
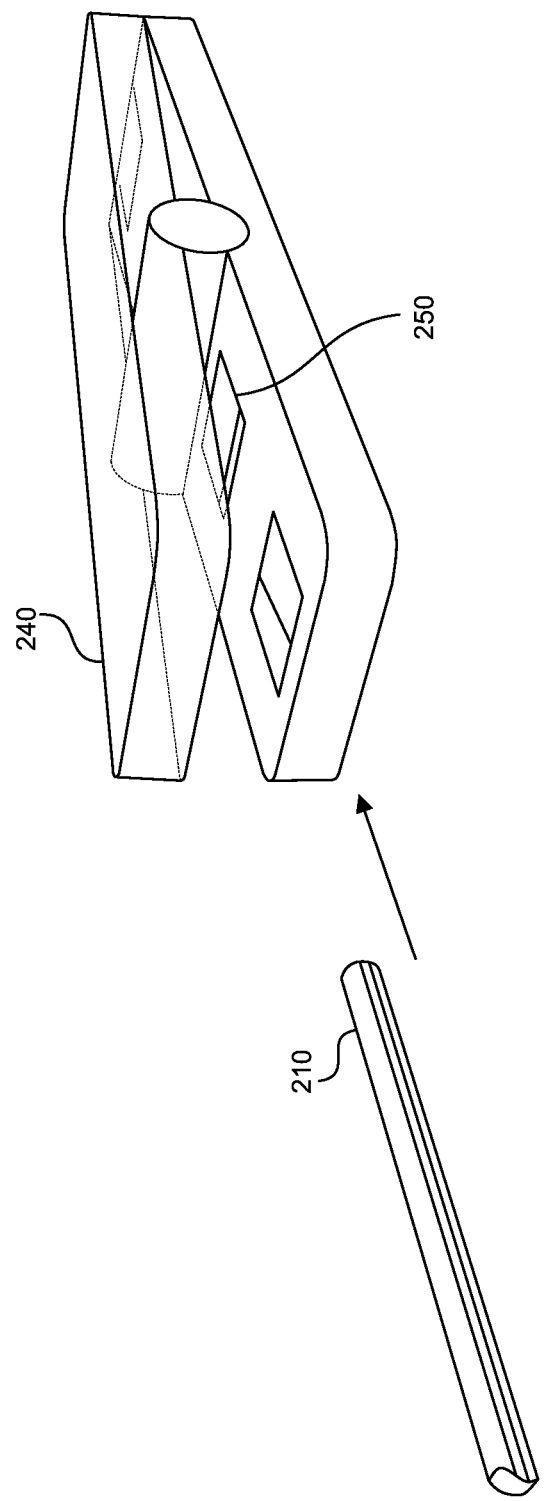

FIGS. 2A-2B show a string engaging with the wearable device, according to one embodiment. The string 210 attached to the tampon 220 can be used to pull the tampon 220 out of the body. The string 210 also encloses a plurality of conductive wires, that when inserted into the wearable device 200, establish an electric contact with the wearable device 200. When the button 230 associated with a wearable device 200 is pressed, a clamp 240 in FIG. 2B disposed within the wearable device 200 opens to allow the string 210 to be inserted inside the clamp 240, through the opening 270. The clamp 240 in FIG. 2B includes an electrical contact 250 in FIG. 2B, which when engaged with the plurality of conductive wires inside the string 210 activates a display 260 associated with a wearable device 200. The display 260 can be an LED that emits lights when the contact between the plurality of conductive wires and the electrical contact 250 is established.

According to one embodiment, the clamp 240 includes a mechanism similar to that of a slide-button flashlight. The wearable device 200 includes slide a button. When the button is slid into a locked position, the clamp 240 locks the string 210 into place, where the conductive wires inside the string 210 establish an electrical contact with a wearable device 200. When the button is slid into an open position, the clamp 240 releases the string 210, and the electrical contact is terminated.

According to another embodiment, the string 210 includes a stiff end, which is not attached to the tampon 220. The stiff end plugs into the wearable device 200 with a small hook or a bump, which fits into a groove inside the wearable device 200, "locking" the string in place.

Additional clamping mechanisms include:
  A circle and/or a circular prism of material which can be tightened to clamp around the incoming tampon string.
  A pair of magnets which seek out and latch onto the tampon string when the string is inserted.
  A pair of magnets which attract the tampon string when the string is inserted.
  A "through-hole" device where the tampon string is inserted into the device, and then comes out the other end. The user can pull on the protruding end to lock the section of the string with the leads into place inside the device. The section of the string with the leads is slightly thicker, then the rest of the string.

In addition, any combination of the two or more clamping mechanisms described herein can also be employed to secure the string inside the wearable device.

Figure 3C:
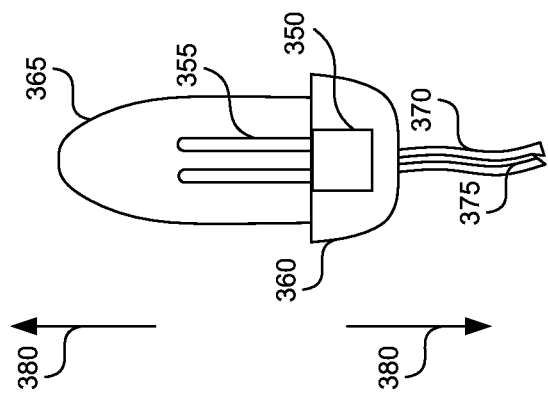
FIG. 3C shows the tampon with an external electronics unit, according to one embodiment.
Figure 3B:
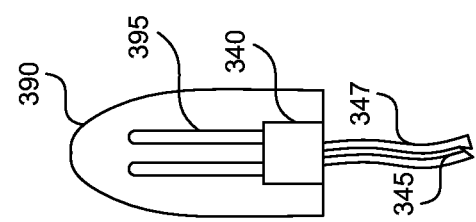
FIG. 3B shows the tampon with an internal sensor and an internal electronic unit, according to another embodiment.
Figure 3A:
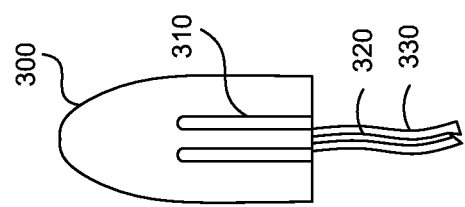
FIG. 3A shows the tampon with an internal sensor, according to one embodiment.

FIG. 3A shows the tampon with an internal sensor, according to one embodiment. The internal sensor includes a probe pair 310 inserted inside the absorbent part of the tampon 300, so that the probe pair 310 does not come in contact with the vaginal walls. The individual probes in the probe pair 310 are spaced apart and do not come into contact with each other. The distance between the probe pair 310 is set during manufacturing. The individual probes in the probe pair 310 can be made of implant grade surgical steel 0.1 millimeter wire.

When the absorbent part of the tampon 300 is dry, the current flowing between the probe pair 310 is low, meaning that the ohmic resistance is high. The conductance between the probe pair 310 when the absorbent part of the tampon 300 is dry is known before the tampon 300 is inserted in the body. As the absorbent part of the tampon 300 receives more blood, the conductance changes, e.g., the ohmic resistance between the probe pair 310 decreases, allowing more electric current to flow between the probe pair 310 because blood is conductive. Thus, as the absorbent part of the tampon 300 gets more saturated, more electric current flows between the probe pair 310. The plurality of conductive wires 320, enclosed in a string 330 attached to the tampon 300, carry the electric current outside of the tampon 300 and into the wearable device.

Alternatively, the saturation of the tampon 300 can be measured using capacitance sensing. When the absorbent part of the tampon 300 is dry, the capacitance is low. As the absorbent part of the tampon 300 receives more blood, the capacitance increases. A single probe can be inserted into the tampon 300 to measure capacitance. As with the resistance-measuring probe(s), this single probe connects to the wearable device, as described herein.

According to another embodiment, each of the conductive wires in the plurality of conductive wires 320 can be enclosed in a single string, attached to the tampon 300. In this case, each string enclosing a conductive wire attaches to the wearable device, and establishes an electrical contact therein.

The wearable device performs initial processing on the data received, such as performing low-pass filtering to obtain a smooth data. The wearable device wirelessly communicates the smooth data and/or the data received to a remote processor for further analysis. When the tampon 300 is disposed of, the conductive wires, and the probe pair are disposed of at the same time.

FIG. 3B shows the tampon with an internal sensor and an internal electronic unit, according to another embodiment. The internal sensor includes the probe pair 395. The individual probes in the probe pair 395 can be made of implant grade surgical steel 0.1 millimeter wire. The probe pair 395 is connected to an internal electronic unit 340. The internal electronic unit 340 receives the data regarding the electric conductivity in the tampon 390 from the probe pair 395. The internal electronic unit 340 can include a processor to analyze the data, such as performing a low-pass filter on the data coming in from the probe pair 395 to create a smooth data. The internal electronic unit 340 includes a wireless transceiver to send the smooth data and/or data to a remote processor for further analysis. The wireless transceiver uses a wireless protocol, such as Bluetooth, to communicate with the remote processor. The internal electronics unit 340 can also connect to a plurality of conductive wires 345 enclosed within the string 347 attached to the tampon 390. The plurality of conductive wires 345 can connect to the wearable device, as described above. When the tampon 390 is disposed of, the internal electronics unit 340 and the probe pair 395 are disposed of at the same time.

FIG. 3C shows the tampon with an external electronics unit, according to one embodiment. The external electronics unit 350 is contained inside a housing 360 disposed at the base of the tampon 365. The housing 360 can be a 3-D printed encasing.

The external electronics unit 350 can include a processor to analyze the data, such as performing a low-pass filter on the data coming in from the probe pair 355 to create a smooth data. The external electronics unit 350 includes a wireless transceiver to send the smooth data and/or data to a remote processor for further analysis. The wireless transceiver uses a wireless protocol, such as Bluetooth, to communicate with the remote processor. The internal electronics unit 350 can also connect to a plurality of conductive wires 375 enclosed within the string 370 attached to the housing 360. The plurality of conductive wires 375 can connect to the wearable device, as described above.

The external electronics unit 350 and the probe pair 355 can detach from the tampon 365 when enough outward force 380 is applied. Thus, the absorbent part of the tampon 365 can be disposed of, while the external electronics unit 350 and the probe pair 355 are preserved. The external electronics unit 350 and the probe pair 355 can be reused in another tampon. When the probe pair 355 is inserted into a tampon, the processor associated with the external electronics unit 350 measures the amount of electronic current inside the dry tampon 365. The processor associated with the external electronics unit 350 stores the measurement as a baseline for comparison with future electronic current measurements. The processor associated with the external electronics unit 350 can communicate the baseline measurement to a remote processor. The absorbent part of the tampon includes a cavity in the shape of the probe pair to allow the probe pair 355 to be inserted into the absorbent part of the tampon 365.

The remote processor can be associated with a mobile device, a wearable device, a computer, a cloud computer, etc. The mobile device can be a tablet, a cell phone, a personal digital assistant, etc. The wearable device can be a watch, a heart rate monitor, a wearable device integrated into clothing, fitbit bracelet, etc. The remote processor performs various functions, such as receiving the smooth data and/or data from the wearable device via the wireless connection, storing the smooth data and/or data in a database to create a historical data associated with the menstrual cycle of the user, and analyzing the smooth data and/or data, and/or the historical data to generate various notifications to the user. In analyzing the data, the remote processor can utilize various machine learning algorithms. The remote processor sends notifications to a display associated with the processor, such as a display associated with the mobile device, a display associated with a wearable device, or a display associated with the computer. The display generates a visual message corresponding to the notification, the visual message comprising at least one of a textual message, an image, a graph, or a video.

Figure 3D:
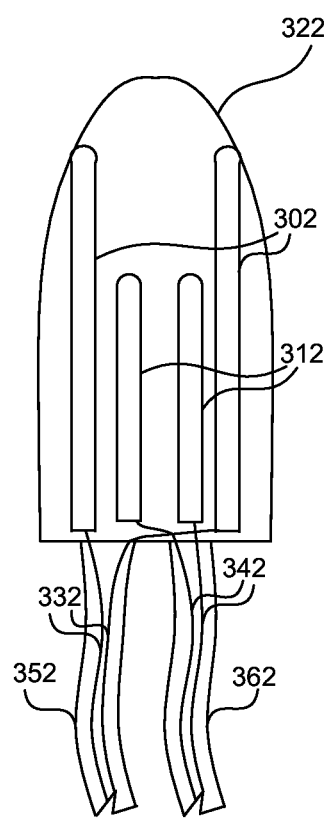
FIG. 3D shows the tampon with a plurality of internal sensors and a plurality of strings, according to one embodiment.

FIG. 3D shows the tampon with a plurality of internal sensors and a plurality of strings, according to one embodiment. The plurality of internal sensors includes plurality of probe pairs 302, 312. Plurality of probe pairs 302, 312 are inserted into the absorbent part 322 of the tampon. A plurality of conductive wires 332 connects to the probe pair 302, while a plurality of conductive wires 342 connects to the probe pair 312. Plurality of conductive wires 332, 342 carry the current between the corresponding plurality of probe pairs 302, 312 outside of the tampon, and into the wearable device. A string 352 encloses the plurality of conductive wires 332, while a string 362 encloses the plurality of conductive wires 342. The plurality of strings 352, 362 can connect to the wearable device, where the plurality of conductive wires 332, 342 establish an electrical contact with the wearable device, as described herein. Various embodiments of the present invention described herein can include a plurality of strings, where one or more strings in the plurality of strings encloses a plurality of conductive wires.

Figure 4A:
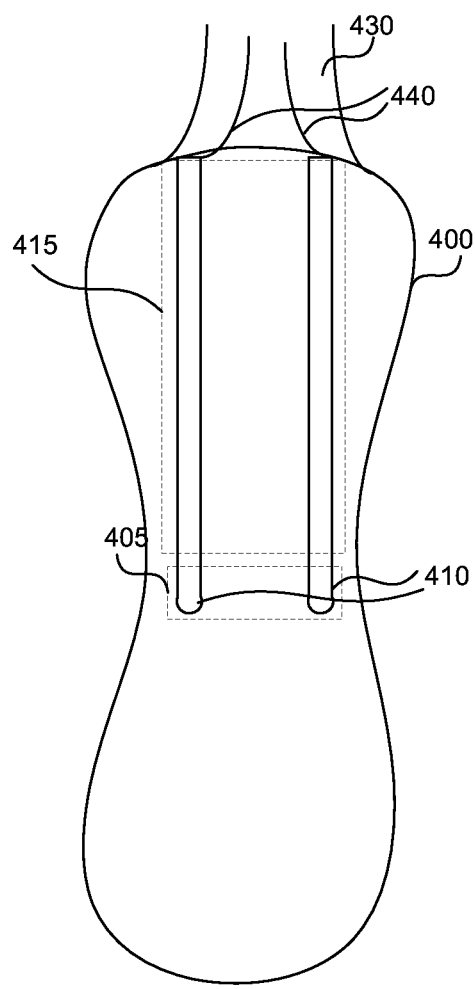
FIG. 4A shows a sanitary napkin with a sensor, according to one embodiment.

FIG. 4A shows a sanitary napkin with a sensor, according to one embodiment. The probe pair 410 is inserted inside the sanitary napkin 400. The individual probes in the probe pair 410 can be made of implant grade surgical steel 0.1 millimeter wire. The probe pair 410 measures the amount of moisture inside the sanitary napkin, based on the ohmic resistance to electric current between the probe pair 410, as described above. The probe pair 410 connects to a plurality of conductive wires 440 enclosed inside the string 430 coming out of the sanitary napkin. The string 430 connects to the wearable device, as described above. Alternatively, a single probe can be inserted to measure capacitance. As with the resistance-measuring probe(s), this single probe connects to the wearable device, as described herein. In various embodiments described herein, the single probe can be inserted to measure capacitance, and thus saturation of the hygiene product.

The tip region 405 associated with the probe pair 410 includes a cathode and an anode, which are made out of an exposed conductor. The base region 415 associated with the probe pair 410 includes a conductor covered with an insulator. The base region 415 is not conductive.

Figure 4B:
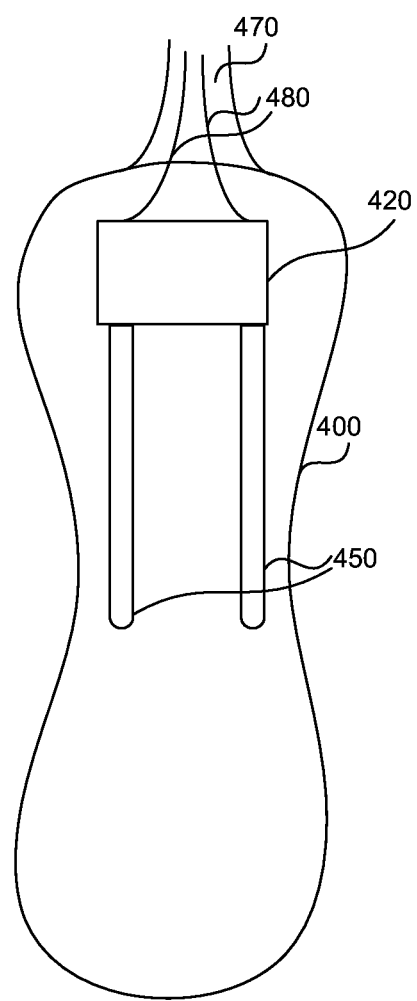
FIG. 4B shows a sanitary napkin with a sensor and an internal electronics unit, according to one embodiment.

FIG. 4B shows a sanitary napkin with a sensor and an internal electronics unit, according to one embodiment. The probe pair 450 is inserted inside the sanitary napkin 400. The individual probes in the probe pair 450 can be made of implant grade surgical steel 0.1 millimeter wire. The probe pair 450 measures the amount of moisture inside the sanitary napkin, based on the ohmic resistance to electric current between the probe pair 450, or the capacitance registered by the probe, as described above. The probe pair 450 connects to an electronics unit 420 disposed within the sanitary napkin 400. The electronics unit 420 communicates wirelessly to a remote processor the data received from the probe pair 450. The electronics unit 420 can also process the data received, such as performing a low-pass filter to create a smooth data, as described above.

In one embodiment, the electronics unit 420 can connect to a plurality of conductive wires 480 enclosed inside the string 470 coming out of the sanitary napkin 400. The string 470 can connect to a wearable device, as described above.

Figure 5:
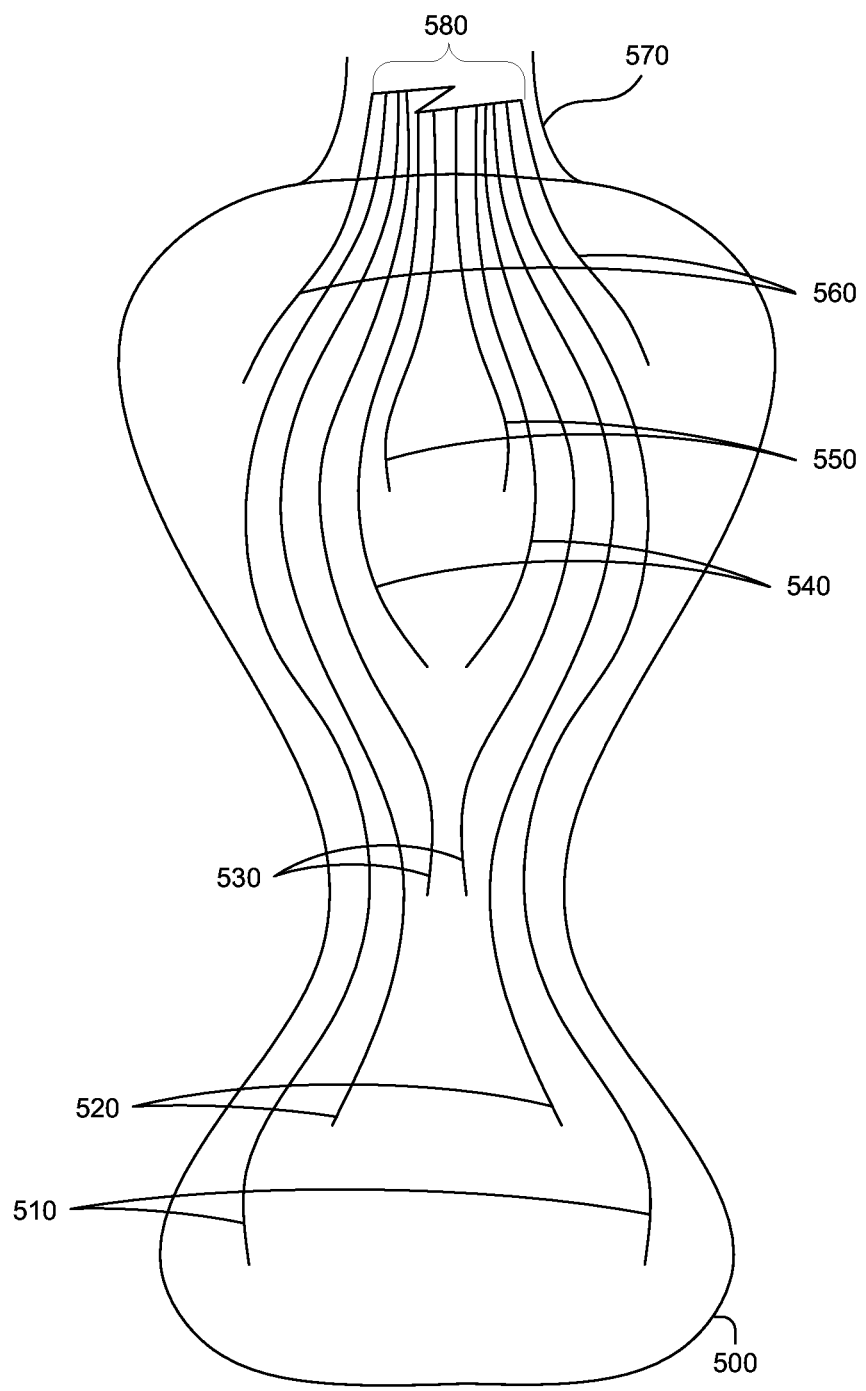
FIG. 5 shows a sanitary napkin with a sensor, according to another embodiment.

FIG. 5 shows a sanitary napkin with a sensor, according to another embodiment. The sanitary napkin 500 includes the sensor, which includes a plurality of probe pairs 510-560, each of which measure an amount of current, and/or ohmic resistance, and/or a capacitance between one or more probes in a probe pair 510-560. The individual probes in the probe pairs 510-560 can be made of implant grade surgical steel 0.1 millimeter wire. The measurements are carried to the wearable device through the plurality of conductive wires 580 enclosed in a string 570 attached to the sanitary napkin 500.

Figure 6:
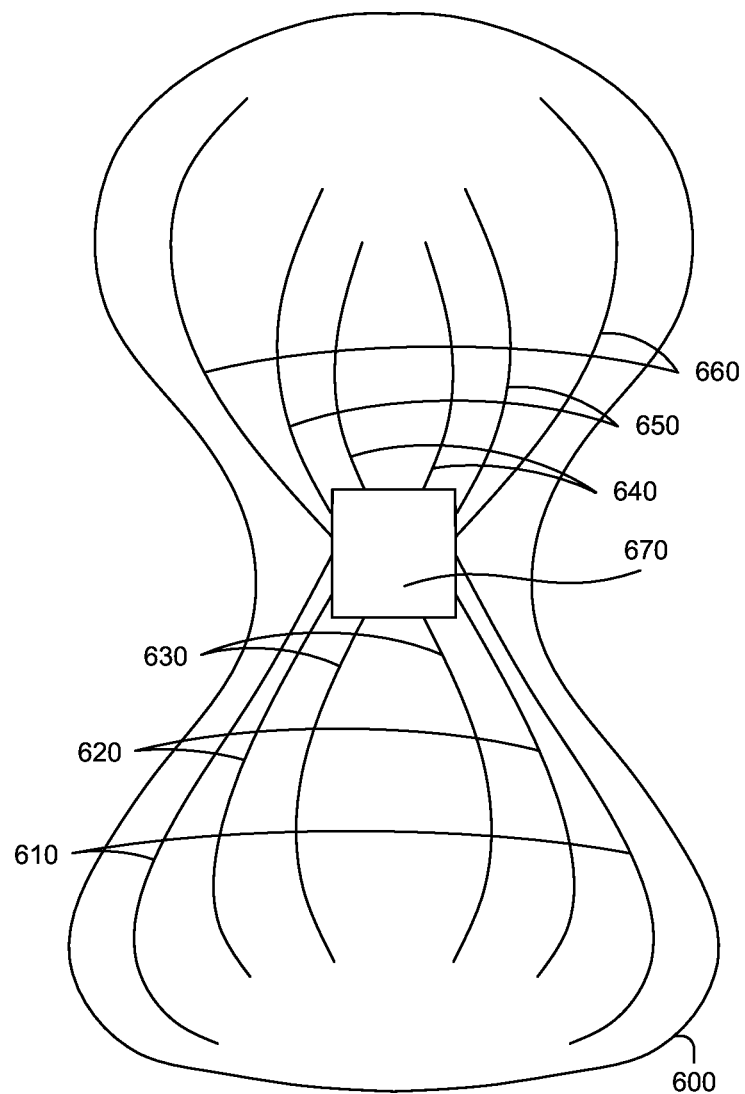
FIG. 6 shows a sanitary napkin with a sensor, according to another embodiment.

FIG. 6 shows a sanitary napkin with a sensor and an internal electronics unit, according to another embodiment. The sanitary napkin 600 includes the sensor and an electronics unit 670. The sensor includes a plurality of probe pairs 610-660 which are connected to the electronics unit 670. The individual probes in the probe pairs 610-660 can be made of implant grade surgical steel 0.1 millimeter wire. The electronics unit 670 gathers data from the probe pairs 610-660. The electronics unit 670 can send the gathered data to a processor, either wirelessly or through a wire connected to the electronics unit 670. The electronics unit 670 can send the gathered data along with the identification (ID) of the probe pair that gathered the data. Alternatively, the electronics unit 670 can process the gathered data, such as performing low-pass filtering on the gathered data to obtain smooth data, or combining the data from the plurality of probe pairs 610-660 into a single measurement representing an amount of saturation of the sanitary napkin. The electronics unit 670 can then communicate the smooth data and/or the single measurement to the remote processor either wirelessly or through a wire connected to the electronics unit 670.

Figure 7A:
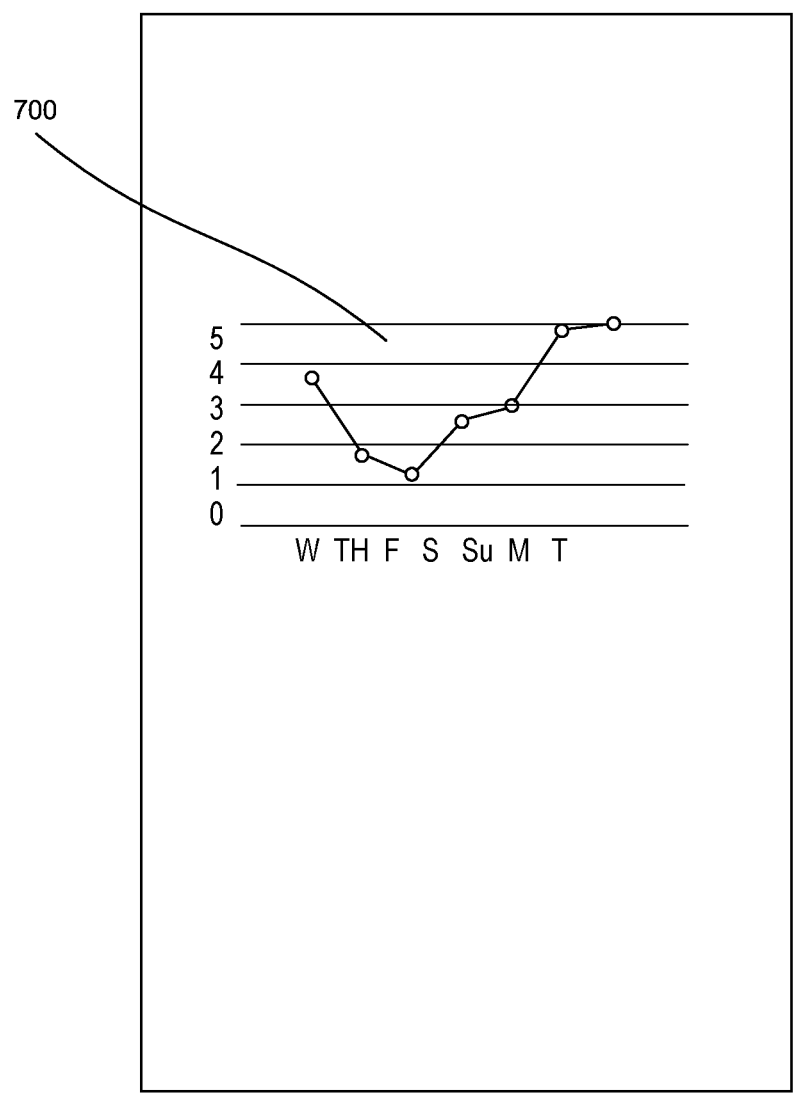
FIGS. 7A-7C show an example of a notification to the user, according to various embodiments.
Figure 7B:
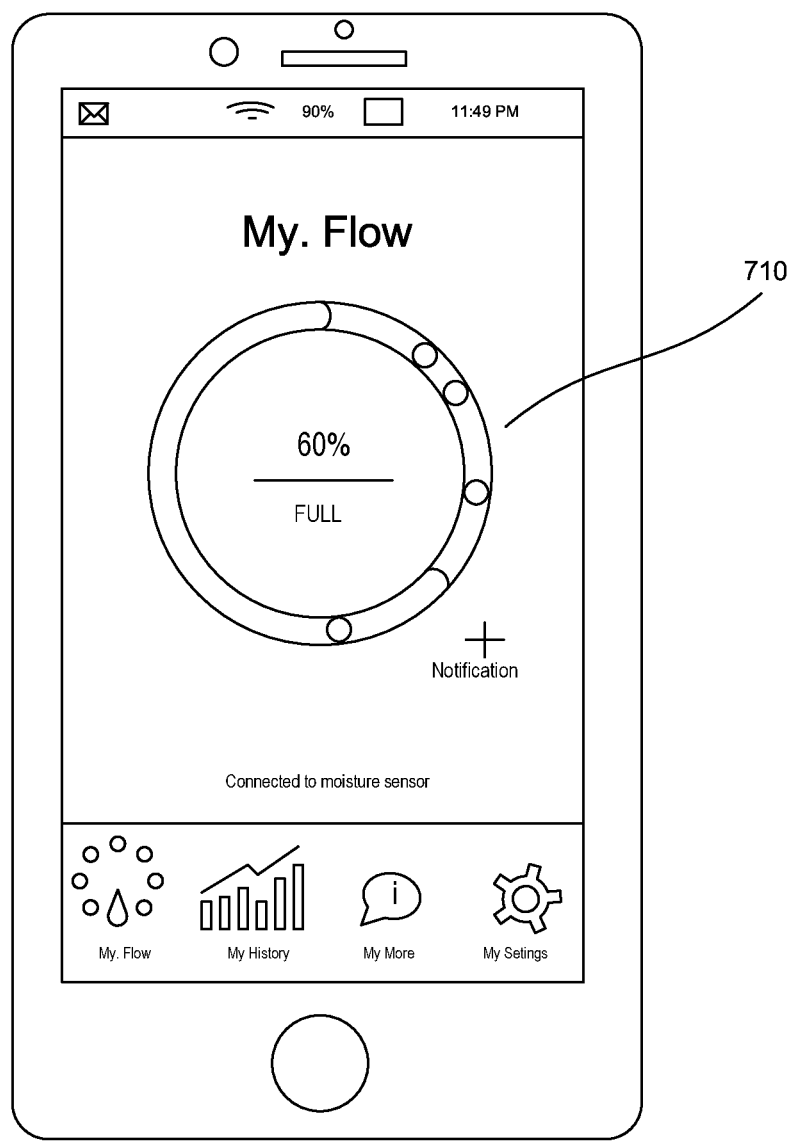
Figure 7C:
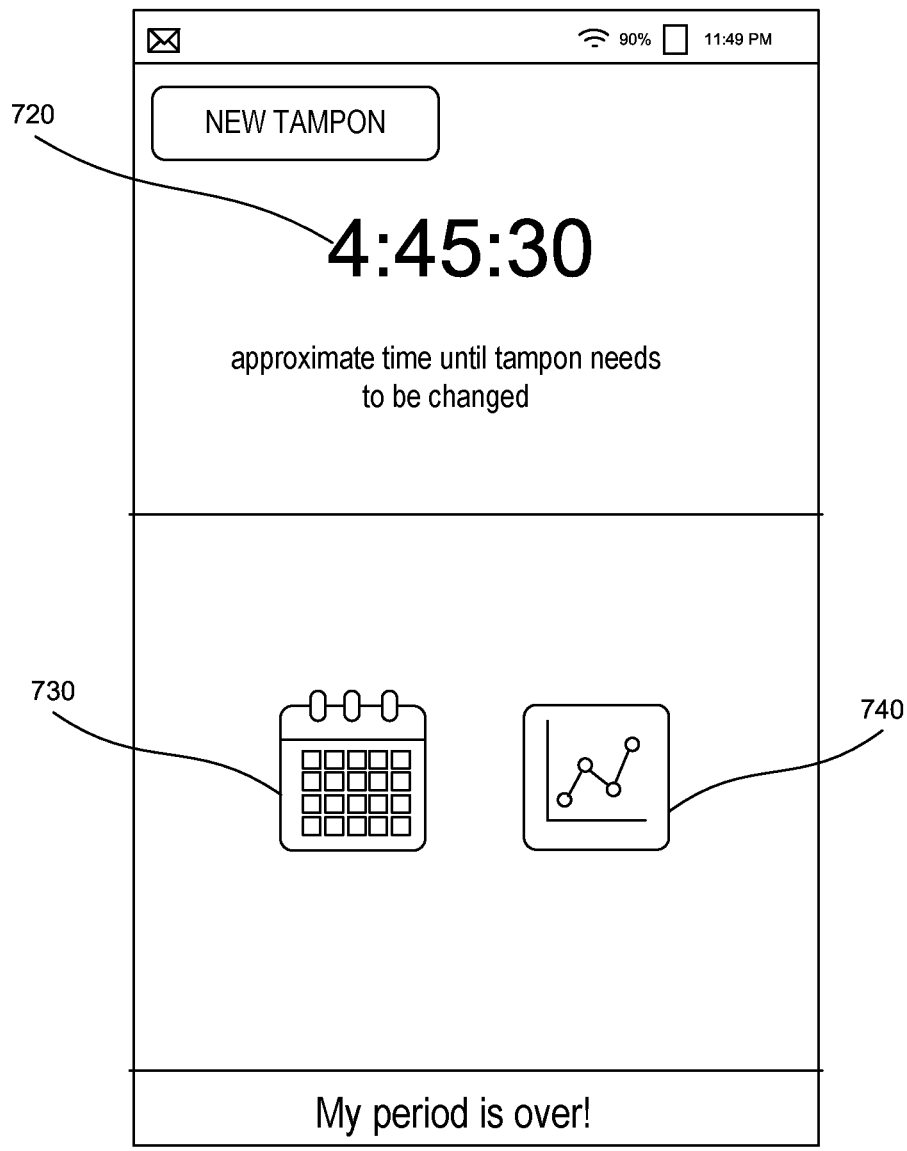

FIGS. 7A-7C show an example of a notification to the user, according to various embodiments. Graph 700 in FIG. 7A represents a correspondence between a day of the week (e.g., Wednesday, Thursday, Friday, Saturday, etc.) and an average amount of time elapsed before the feminine hygiene product is fully saturated. Display 710 in FIG. 7B associated with the mobile device shows an amount of saturation associated with the feminine hygiene product. Message 720 in FIG. 7C associated with the mobile device shows an approximate time when the feminine hygiene product needs to be changed. Additional notifications 730, 740 in FIG. 7C can be shown to the user, such as an expected start and end of the next menstrual cycle, an alert to change the feminine hygiene product, an expected day when the blood flow will be the heaviest, etc. In addition, the notification can be integrated with various third-party health applications, such as Google health applications, and/or Apple health applications.

Figure 8A:
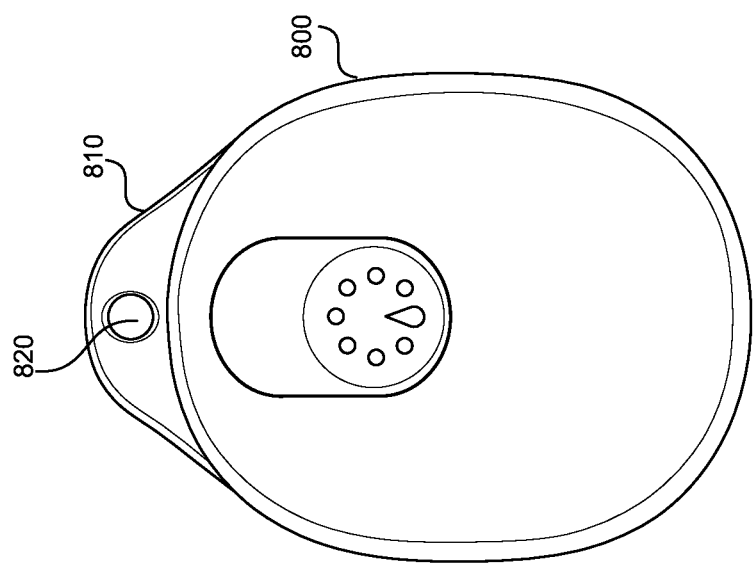
FIGS. 8A-8C show the wearable device, according to one embodiment.
Figure 8B:
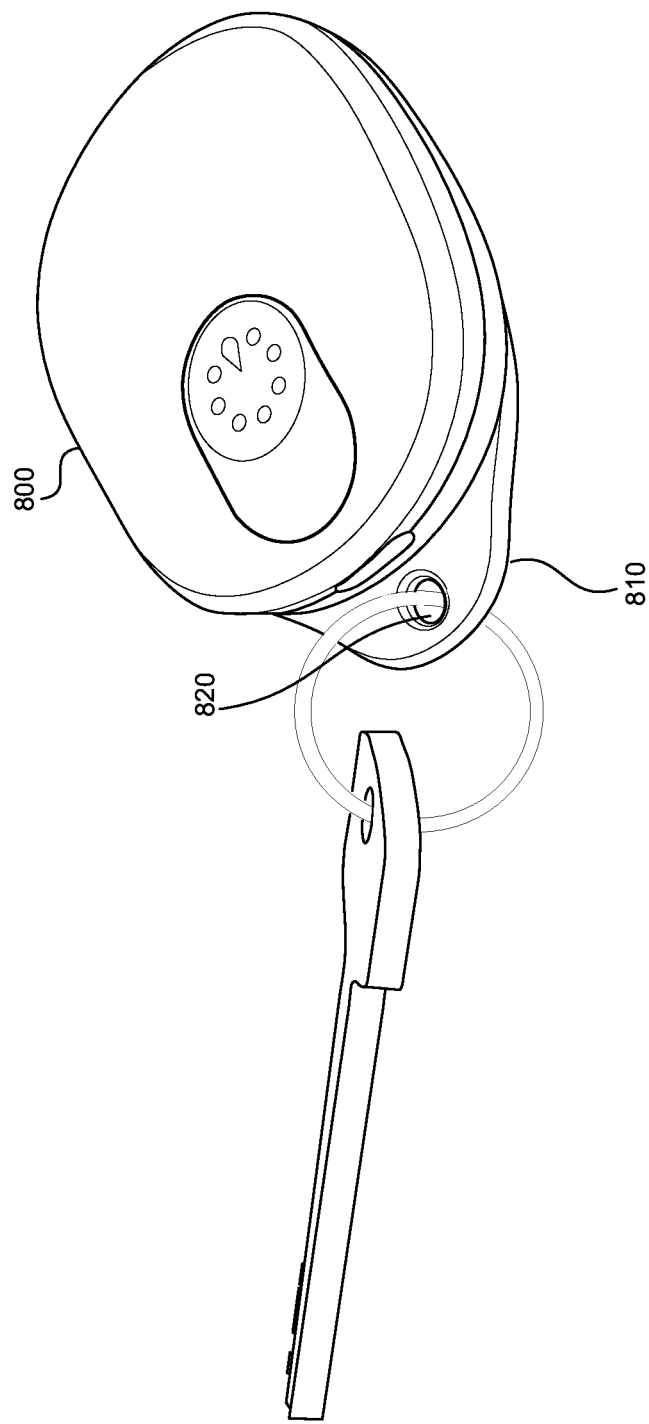
Figure 8C:
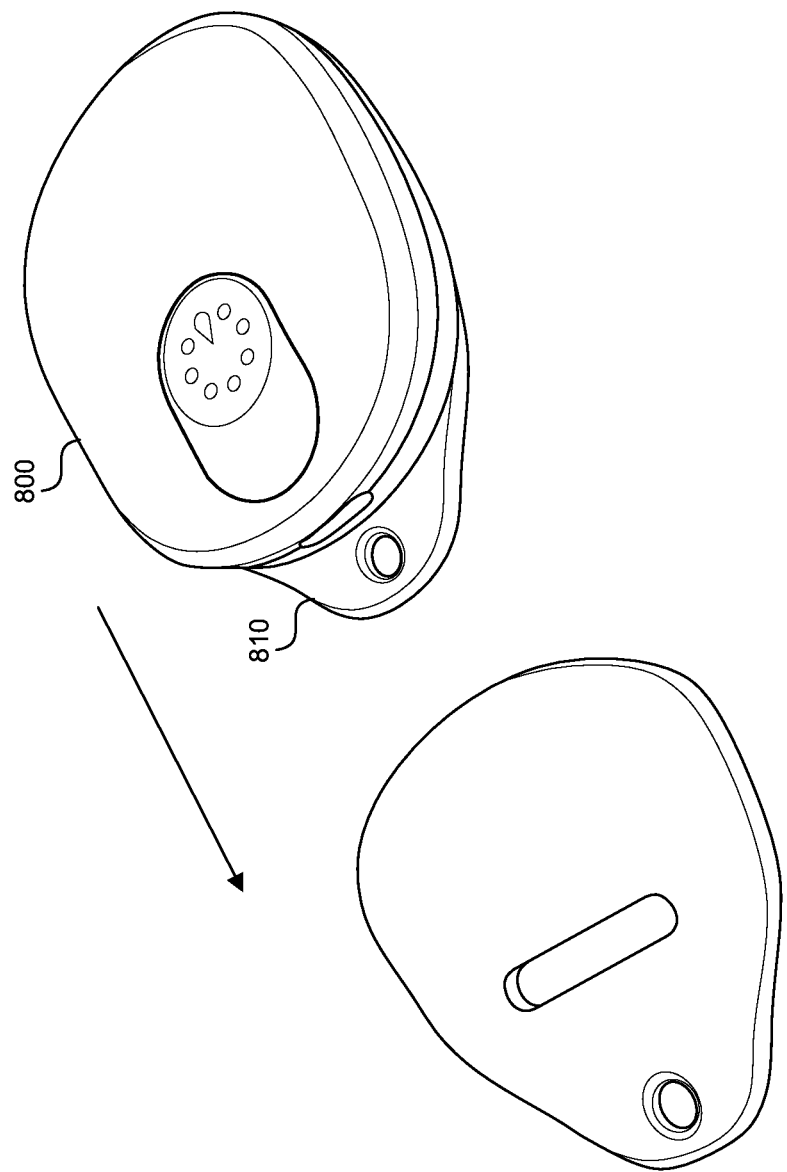

FIGS. 8A-8C show the wearable device, according to one embodiment. The wearable device 800 includes a removable keychain attachment member 810. The keychain attachment member 810 includes a hole 820 which allows a keychain loop to attach to the wearable device 800, as shown in FIG. 8B. The keychain attachment member 810 can be removed from the wearable device 800, as shown in FIG. 8C.

Figure 9:
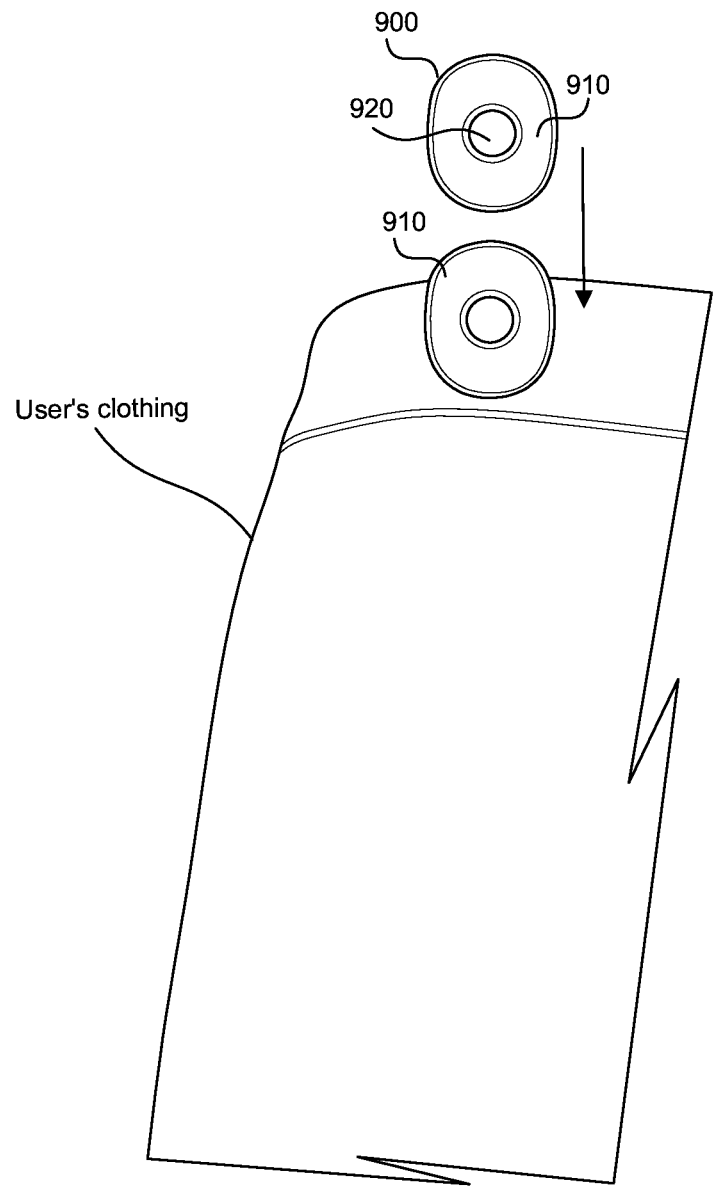
FIG. 9 shows the wearable device attached to a piece of clothing associated with the user, according to one embodiment.

FIG. 9 shows the wearable device attached to a piece of clothing associated with the user, according to one embodiment. A clip 910 disposed on the back side associated with a wearable device 900 is configured to attach to the piece of clothing associated with the user, such as pants, a skirt, a belt, a pocket, an undergarment, etc. The clip 910 is discreetly disposed on the back side 920 associated with a wearable device 900. The clip 910 does not have any markings and is discrete in appearance. The clip 910 can attach to the piece of clothing regardless whether the keychain attachment member is removed or attached to the wearable device 900.

A person of ordinary skill in the art will recognize that the technology disclosed herein can be applied to monitor additional physiological phenomena associated with a user. The physiological phenomena includes secretions such as an amount of urination, an amount of defecation, an amount of penile and vaginal discharge, etc. The sensor can be disposed inside a child diaper, an adult diaper, training pants, incontinence pads for men and women, a tampon, a panty liner, a sanitary napkin, a sanitary brief, a menstrual cup, etc.

Figure 10:
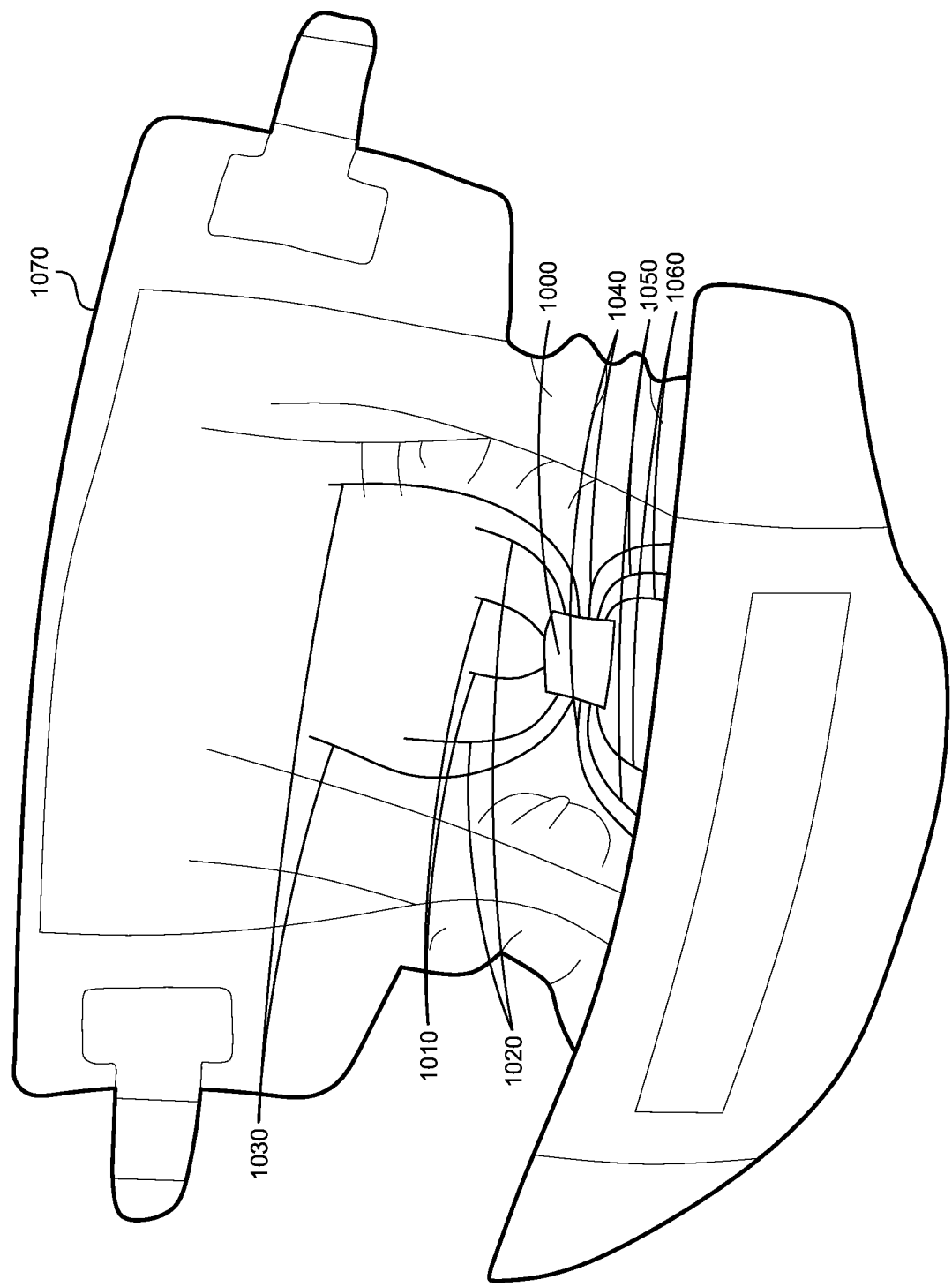
FIG. 10 shows a sensor disposed within a diaper, according to one embodiment.

FIG. 10 shows a sensor disposed within a diaper, according to one embodiment. The sensor includes probe pairs 1010-1060. The individual probes in the probe pairs 1010-1060 can be made of implant grade surgical steel 0.1 millimeter wire. The probe pairs 1010-1060 are configured to measure the amount of moisture by measuring changes in an electric conductivity between the probe pairs 1010-1060. As explained above, the higher the moisture, the higher the electric conductivity between probe pairs 1010-1060 because the moisture acts as a conductor. The probe pairs 1010-1030 disposed on the back of the diaper 1070 can be configured to measure an amount of defecation, while the probe pairs 1040-1060 disposed on the front of the diaper 1070 can be configured to measure an amount of urination.

An electronics unit 1000 receives data from the probe pairs 1010-1060. The electronics unit 1000 can send the gathered data to a processor, either wirelessly or through a wire connected to the electronics unit 1000. The electronics unit 1000 can send to the processor, in addition to the gathered data, an identification (ID) associated with the probe pair corresponding to the collected data. Further, the electronics unit 1000 can send to the processor information associating the probe ID with the front or the back of the diaper 1070, or associating the probe ID with the physiological phenomena, such as urination and/or defecation.

The electronics unit 1000 can process the gathered data, such as performing low-pass filtering on the gathered data to obtain smooth data, combining the data from the plurality of probe pairs 1010-1060 into a single measurement representing an amount of saturation of the diaper, or calculating an amount of urination and an amount of defecation and sending the amount of urination and the amount of defecation to the processor. Electronics unit 1000 can then communicate the smooth data and/or the single measurement to the processor either wirelessly or through a wire connected to the electronics unit 1000.

In addition to the probe pairs, the sensor can include a piezo sensor, a temperature sensor, etc.

Figure 11:
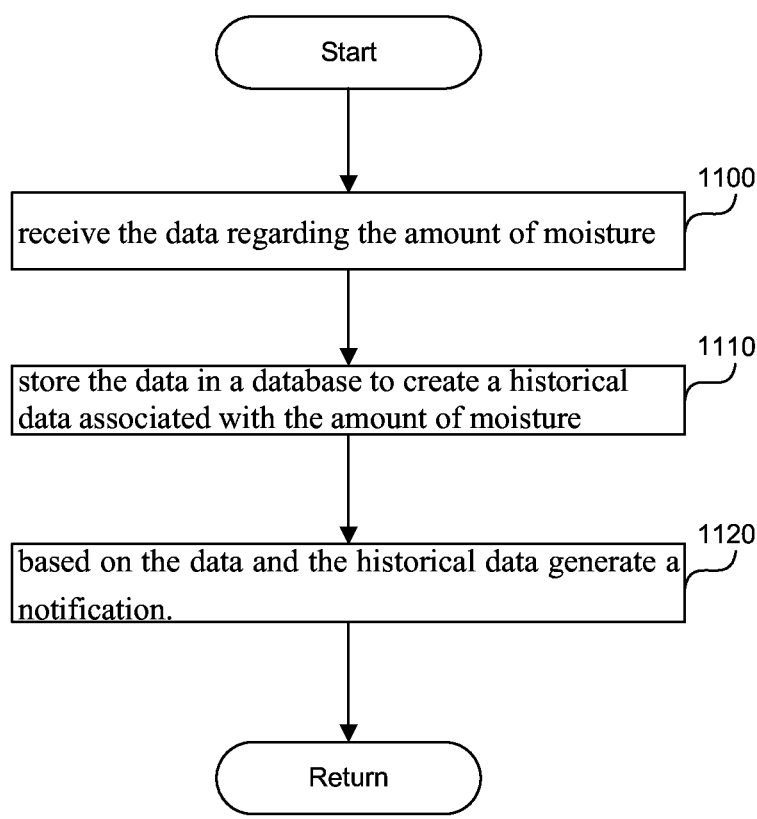
FIG. 11 is a flowchart of steps taken by the processor communicatively coupled to the sensor, according to one embodiment.

FIG. 11 is a flowchart of steps taken by the processor communicatively coupled to the sensor, according to one embodiment. In step 1100, the processor receives the data regarding the amount of moisture. In step 1110, the processor stores the data in a database to create a historical data associated with the amount of moisture. In step 1120, based on the data and the historical data, the processor generates a notification, the notification comprising at least one of the notification to change the hygiene product or the notification that the user may be sick. The notification can be sent to a caretaker and/or the user. For example, a notification that a baby's diaper is at least 80% full can be sent to a mother, or the notification to change an adult diaper can be sent to the adult's caretaker.

In addition, the processor can compare the data received and the historical data to detect an abnormal fluctuation between the historical data and the received data. The abnormal fluctuation is outside of a normal fluctuation range associated with the historical data. For example, if the normal fluctuation range for the number of times a baby urinates is between four and eight times a day, an abnormal fluctuation is when the baby urinates two times a day. When the abnormal fluctuation is detected, the processor sends the notification to a responsible person that the user may be sick (e.g., the user may be having a urinary tract infection). The responsible person can be the user, or the responsible person can be a caretaker associated with the user, such as the baby's mother.

Figure 12:
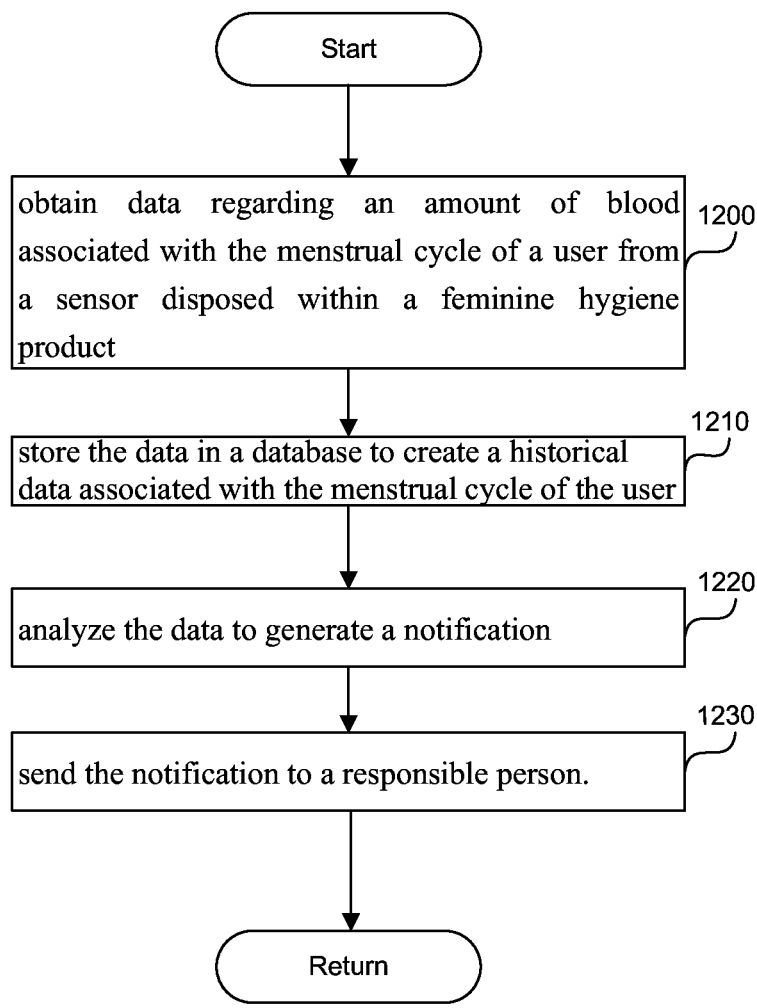
FIG. 12 is a flowchart of a method to monitor a blood flow during a menstrual cycle of a user, according to one embodiment.

FIG. 12 is a flowchart of a method to monitor a blood flow during a menstrual cycle of a user, according to one embodiment. In step 1200, the processor obtains data regarding an amount of blood associated with the menstrual cycle of the user from a sensor disposed within a feminine hygiene product. In step 1210, the processor stores the data in a database to create a historical data associated with the menstrual cycle of the user.

In step 1220, the processor analyzes the data to generate a notification. The notification includes at least one of: a message to change the feminine hygiene product, a prediction of a start date and an end date associated with a next menstrual cycle, the message that the user may be sick, an amount of saturation associated with the feminine hygiene product, a graph of an amount of time passed before the feminine hygiene product is full versus day of the week, an expected day when the menstrual flow will be the heaviest, a countdown timer that warns when the feminine hygiene product should be changed based on how long the previous feminine hygiene product took to fill up, etc.

The processor can make predictions of the heaviest flow day, or the start and end dates associated with the next menstrual cycle based on weighted averages. To predict the start and end dates of the next menstrual cycle, the processor can use weighted averages, machine learning algorithms, etc. In addition, other biological phenomena, such as body temperature, can be taken into account to predict the start and end dates of the next menstrual. For example, to predict the start and end dates of the next menstrual cycle, the processor determines the time between the previous six cycles and calculates a weighted average, where the weight is correlated to how recent the menstrual cycle is. For example, assume the time between the last six menstrual cycles lasted 23, 26, 30, 32, and 28 days, where the time between the last cycle in the next-to-last cycle lasted 28 days. The processor calculates the time to the next cycle to be equal to 0.4*23+0.25*26+0.2*30+0.1*32+0.05*28=26.3. The processor then rounds the results to the nearest integer number of days, thus obtaining 26 days to the next cycle.

Similarly, the weighted averages approach, or machine learning algorithms can be used to predict the heaviest flow day. In addition, other biological phenomena, such as body temperature, can be taken into account to predict the heaviest flow day. For example, assume the heaviest flow day in the last three menstrual cycles was day 2, day 3, and day 1. The processor calculates that the heaviest flow day in the next menstrual cycle to be equal to 0.5*2+0.3*3+0.2*1=2.1 the processor then rounds the result to the nearest integer number of days, thus obtaining that day 2 will be the heaviest in the next menstrual cycle.

In step 1230, the processor sends the notification to a responsible person. The responsible person can be the user, a caretaker associated with the user, and/or a third party that has been given access to the user data, such as a doctor, the user's partner, etc. For example, the processor can receive an authorization from the user to share the data and/or the historical data with a third party device associated with the third party. The user can authorize sharing of a specified time window of historical data, full historical data, and/or currently measured data.

According to one embodiment, the processor can determine whether the feminine hygiene product is within a predefined threshold of being fully saturated. For example, if the feminine hygiene product is 60% saturated, the processor sends a notification to the responsible person to change the feminine hygiene product, such as a notification including a time when the feminine hygiene product is expected to be fully saturated. In another embodiment, the processor displays a constant update of the present saturation of the feminine hygiene product.

The processor can also obtain the time elapsed since the feminine hygiene product has been in use. When the time elapsed is above a specified threshold, the processor sends the notification to the responsible person to change the feminine hygiene product. For example, if the feminine hygiene product does not saturate after eight hours to the level that generates a notification that the feminine hygiene product is saturated, the processor generates a notification to the user to change the tampon based on current industry prevention standards against toxic shock syndrome.

In various embodiments, the processor can generate a plurality of calendar entries associated with the start date and the end date of the next menstrual cycle, and display the plurality of calendar entries in a calendar. Based on the historical data, on a given day, the processor calculates an average amount of time elapsed before the feminine hygiene product is fully saturated. For example, the processor calculates an average amount of time the feminine hygiene product takes to be saturated on day 1, on day 2, on day 3, etc. for each day of the menstrual cycle. The processor then generates a graph representing a correspondence between the day of the menstrual cycle and the average amount of time elapsed before the feminine hygiene product is fully saturated. The graph can be a plot of number of hours versus days of the week, number of hours versus dates, number of hours versus day of the menstrual cycle (such as day 1, day 2, day 3), etc.

The processor can detect an abnormal fluctuation between the historical data and the data. The abnormal fluctuation is outside of a normal fluctuation range associated with the historical data. For example, if the normal fluctuation range for the number of hours the feminine hygiene product takes to fill up on day 1 is between 4 and 8 hours, an abnormal fluctuation is when the feminine hygiene product fills up in 2 hours. When the abnormal fluctuation is detected, the processor sends the notification to a responsible person that the user may be sick, such as, the user may be having a hormone imbalance, a dysfunction of the ovaries, a uterine fibroid, a polyp, adenomyosis, etc. The responsible person can be the user, a caretaker associated with the user, or the user's partner.

In various embodiments disclosed herein, there can be one or more probe pairs disposed within the hygiene product.

System

Figure 13:
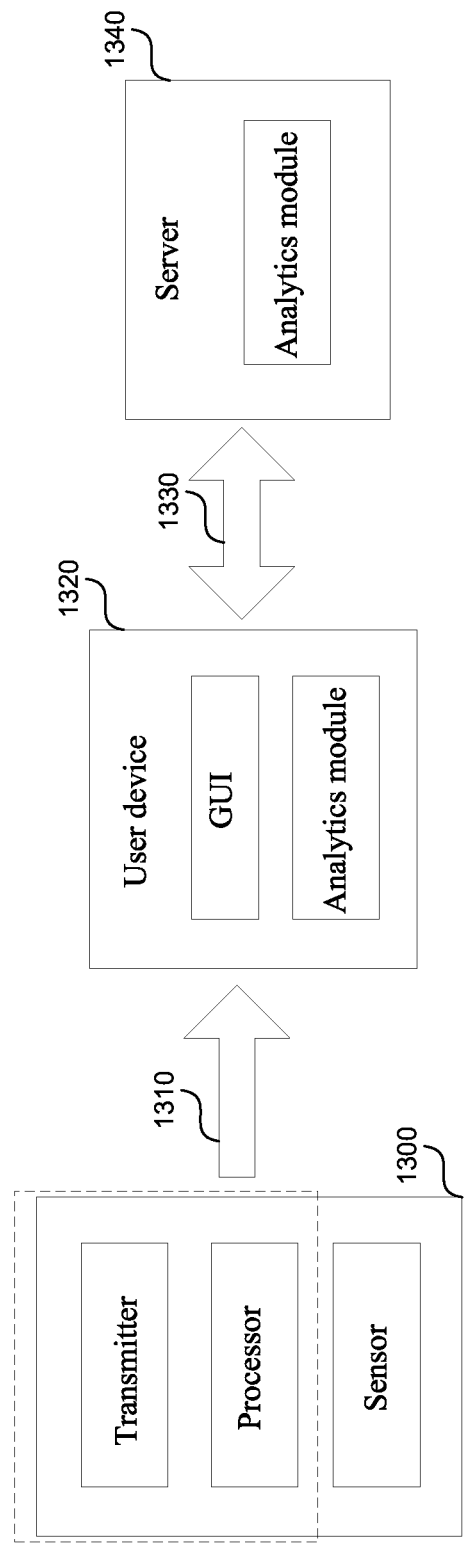
FIG. 13 is a diagrammatic representation of a machine in the example form of a system within which a set of instructions, for causing the machine to perform any one or more of the methodologies or modules discussed herein, may be executed.

FIG. 13 is a diagrammatic representation of a machine in the example form of a system within which a set of instructions, for causing the machine to perform any one or more of the methodologies or modules discussed herein, may be executed. The system includes a subsystem 1300, a user device 1320, and a server 1340.

The subsystem 1300 includes a sensor, a transmitter, and a processor. The sensor is inserted into a hygiene product, as disclosed herein. The transmitter and the processor can also be included in the hygiene product, or they can be part of a separate device, such as a wearable device, a mobile device, a personal digital assistant, etc., or a combination of two or more of these. The processor can be, for example, a microcontroller, a conventional microprocessor such as an Intel Pentium microprocessor or a Motorola power PC microprocessor, etc. The processor performs various operations on the data received from the sensor, such as performing a low-pass filter operation. The transmitter communicates to the user device 1320 using a wireless network 1310.

The user device 1320 comprises a display including a graphical user interface (GUI), and an analytics module. The GUI displays various information regarding the observed human physiological phenomena as described herein. The analytics module can perform the various methodologies discussed herein. The user device 1320 includes a processor for running the analytics module, and a memory associated with the processor. The analytics module can be a stand-alone, and/or can be integrated with a third-party software, such as Google health applications, and/or Apple health applications. The memory is coupled to the processor by, for example, a bus. The memory can include, by way of example but not limitation, random access memory (RAM), such as dynamic RAM (DRAM) and static RAM (SRAM), etc. The memory can be local, remote, or distributed, such as a local database, remote database, or a distributed database. The user device 1320 can be a cell phone, a tablet, a wearable, a desktop computer, a laptop computer, a game console, a set-top box, a blackberry, etc. The user device 1320 communicates to the server 1340 using a wireless network 1330.

The server 1340 includes an analytics module. The analytics module can perform the various methodologies discussed herein. The server 1340 includes a processor for running the analytics module, and a memory associated with the processor. The memory can include, by way of example but not limitation, random access memory (RAM), such as dynamic RAM (DRAM) and static RAM (SRAM), RAID (redundant array of independent disks), etc. The memory can be local, remote, or distributed, such as a local database, remote database, or a distributed database. The server 1340 can be implemented in hardware and/or in software. The server 1340 can include a database server, a file server, a mail server, a print server, a Web server, a game server, an application server, etc. The server 1340 can be part of a cloud computing system.

The wireless networks 1310 and/or 1330 may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling others skilled in the relevant art to understand the claimed subject matter, the various embodiments, and the various modifications that are suited to the particular uses contemplated.

While embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Although the above Detailed Description describes certain embodiments and the best mode contemplated, no matter how detailed the above appears in text, the embodiments can be practiced in many ways. Details of the systems and methods may vary considerably in their implementation details, while still being encompassed by the specification. As noted above, particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless those terms are explicitly defined herein. Accordingly, the actual scope of the invention encompasses not only the disclosed embodiments, but also all equivalent ways of practicing or implementing the embodiments under the claims.

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which is set forth in the following claims.

The invention claimed is:

1. A feminine hygiene product to monitor blood flow during a menstrual cycle of a user, the feminine hygiene product comprising:
   an absorbent part, the absorbent part configured to collect blood;
   a wetness sensor disposed within the absorbent part, the sensor specially configured to gather data regarding an amount of blood associated with the menstrual cycle of the user;
   a string attached to the absorbent part and to the sensor, the string enclosing a plurality of conductive wires; and
   a wearable device having a body and removably coupled to the string and to the sensor, the wearable device including a processor configured to:
      (i) receive the data from the sensor regarding the amount of blood;
      (ii) store the data in a database to create historical data associated with the menstrual cycle of the user;
      (iii) based on the historical data, calculate an average amount of time elapsed before the feminine hygiene product is fully saturated on a day associated with the menstrual cycle;
      (iv) generate a graph representing a correspondence between the average amount of time elapsed before the feminine hygiene product is fully saturated in the day associated with the menstrual cycle;
      (v) generate a notification comprising the generated graph and at least one of a message to change the feminine hygiene product, a start date and an end date associated with a next menstrual cycle, and a message that the user may be sick; and
      (vi) transmit the notification over a wireless network to a user device distinct from the wearable device.

2. The feminine hygiene product of claim 1, the wearable device further comprising a display configured to notify the user when the connection between the plurality of conductive wires and the string is established.

3. The feminine hygiene product of claim 1, the sensor comprising a probe pair inserted inside the feminine hygiene product, which is oriented in a parallel configuration inside the absorbent part, the probe pair specially configured to measure the amount of blood by measuring at least one of changes in an ohmic resistance between the probe pair, and changes in a capacitance observed by one or more probes, wherein the changes in the ohmic resistance are negatively correlated to changes in moisture between the probe pair, and wherein the changes in the capacitance are positively correlated to changes in moisture in the absorbent part.

4. The feminine hygiene product of claim 1, further comprising a smartphone display communicatively coupled to the wearable device, the display configured to generate a visual message corresponding to the notification, the visual message comprising at least one of a textual message, an image, a graph, or a video.

5. The feminine hygiene product of claim 1, the feminine hygiene product comprising a tampon, a menstrual cup, a panty liner, or a sanitary napkin.

6. The feminine hygiene product of claim 1, the wearable device further comprising a removable keychain attachment member.

7. The feminine hygiene product of claim 1, the wearable device comprising a clip configured to attach to a piece of clothing associated with the user.

8. A feminine hygiene product comprising:
   a wetness sensor disposed within the feminine hygiene product, the sensor specially configured to gather data regarding an amount of blood associated with a menstrual cycle of a user; and
   a computing device communicatively coupled to the sensor, the computing device including a processor configured to:
      (i) receive the data regarding the amount of blood;
      (ii) store the data in a database to create historical data associated with the menstrual cycle of the user;
      (iii) based on the historical data, calculate an average amount of time elapsed before the feminine hygiene product is fully saturated on a day associated with the menstrual cycle;
      (iv) generate a graph representing a correspondence between the average amount of time elapsed before the feminine hygiene product is fully saturated in the day associated with the menstrual cycle;
      (v) generate a notification comprising the generated graph and at least one of a message to change the feminine hygiene product, a start date and an end date associated with a next menstrual cycle, and a message that the user may be sick; and
      (vi) transmit the notification over a wireless network to a user device distinct from the computing device.

9. The feminine hygiene product of claim 8, the sensor comprising a probe pair inserted inside the feminine hygiene product, the probe pair configured to measure the amount of blood by measuring changes in an electric conductivity between the probe pair, wherein the changes in the electric conductivity are due to changes in moisture between the probe pair, the probe pair oriented in a parallel configuration inside the absorbent article.

10. The feminine hygiene product of claim 8, the sensor configured to:
    detach from the feminine hygiene product when an outward force is applied to the sensor; and
    re-attach to the feminine hygiene product when an inward force is applied.

11. The feminine hygiene product of claim 8, the feminine hygiene product comprising a tampon, a menstrual cup, a panty liner, or a sanitary napkin.

12. The feminine hygiene product of claim 8, the processor coupled to the sensor via a wireless communication protocol.

13. The feminine hygiene product of claim 8, wherein the computing device is a mobile device.

14. The feminine hygiene product of claim 8, wherein the computing device is a wearable device.

15. The feminine hygiene product of claim 8, wherein the computing device comprises a display and the display is configured to generate a visual message corresponding to the notification, the visual message comprising at least one of a textual message, an image, or a video.

16. A method to monitor blood flow during a menstrual cycle of a user, performed at a computing device having one or more processors and memory, the method comprising:
  obtaining data regarding an amount of blood associated with the menstrual cycle of the user from a sensor disposed within a feminine hygiene product;
  storing the data in a database to create historical data associated with the menstrual cycle of the user;
  based on the historical data, calculating an average amount of time elapsed before the feminine hygiene product is fully saturated on a day associated with the menstrual cycle;
  generating a graph representing a correspondence between the average amount of time elapsed before the feminine hygiene product is fully saturated in the day associated with the menstrual cycle;
  generating a notification comprising the generated graph and at least one of a message to change the feminine hygiene product, a start date and an end date associated with a next menstrual cycle, and a message that the user may be sick; and
  transmitting the notification over a wireless network to a user device distinct from the computing device.

17. The method of claim 16, further comprising:
  based on the data, determining whether the feminine hygiene product is within a predefined threshold of being fully saturated; and
  when the feminine hygiene product is within the predefined threshold, sending the notification to the user device to change the feminine hygiene product, wherein the notification comprises a time when the feminine hygiene product is expected to be fully saturated.

18. The method of claim 16, further comprising:
  obtaining a time elapsed since the feminine hygiene product has been in use; and
  when the time elapsed is above a specified threshold, sending the notification to the user device to change the feminine hygiene product.

19. The method of claim 16, said analyzing the data comprising:
  based on the historical data, predicting the start date and the end date associated with the next menstrual cycle.

20. The method of claim 19, comprising:
  generating a plurality of calendar entries associated with the start date and the end date; and displaying the plurality of calendar entries in a calendar.

21. The method of claim 16, further comprising:
  detecting an abnormal fluctuation between the historical data and the data, wherein the abnormal fluctuation is outside of a normal fluctuation range associated with the historical data; and
  when the abnormal fluctuation is detected, sending the notification to the user device that the user may be sick.

22. The method of claim 16, further comprising:
  receiving an authorization from the user to share the historical data with a third party device.

* * * * *